United States Patent [19]

Gondra et al.

[11] Patent Number: 4,778,783
[45] Date of Patent: Oct. 18, 1988

[54] CREAM OR GEL FOR PROLONGING THE EFFECT OF PERFUME-FRAGRANCE ON A PERSON

[75] Inventors: Elizabeth Gondra, 612 Lavergne, Wilmette, Ill. 60091; Blanca A. White, Chicago, Ill.

[73] Assignee: Elizabeth Gondra, Wilmette, Ill.

[21] Appl. No.: 22,563

[22] Filed: Mar. 6, 1987

[51] Int. Cl.$^4$ .............................................. A61K 7/46
[52] U.S. Cl. ............................................ 512/2; 512/3; 514/847; 514/873; 514/894
[58] Field of Search ...................... 252/522 R; 514/847, 514/873, 894; 512/12, 2, 3

[56] References Cited

U.S. PATENT DOCUMENTS

| | | | |
|---|---|---|---|
| 3,939,099 | 2/1976 | Tusa et al. | 252/522 R |
| 4,067,824 | 1/1978 | Teng et al. | 252/522 R |
| 4,264,478 | 4/1981 | Seldne | 252/522 R |
| 4,362,841 | 12/1982 | Minatono et al. | 524/531 |
| 4,368,187 | 1/1983 | Flom et al. | 424/81 |
| 4,424,234 | 1/1984 | Alderson et al. | 514/873 X |
| 4,474,912 | 10/1984 | Ozmeral et al. | 523/337 |

OTHER PUBLICATIONS

The Merck Index, 10th Ed (1983), 8618–8619.
Rybczynska, Chem. Abs., vol. 64 (1966), 17351(d).
The Condensed Chemical Dictionary, 8th Ed, (1971) 391.

Primary Examiner—Werren B. Lone
Attorney, Agent, or Firm—Milton S. Gerstein

[57] ABSTRACT

A compound cream or gel for application onto the skin of a person before the application of perfume or cologne that prolongs and enhances the fragrance of the perfume or cologne on the person. The cream consists of a large-chained, hydrocarbon in the lipid family in the amount of between approximately 5% and 10%, with the outer ingredients consisting of emulsifying wax in the amount of approximately 11% to make the cream thick, as well as appropriate emollients, preservatives and water solvent. In the preferred form, the hydrocarbon lipid is squalane or squalene.

2 Claims, No Drawings

CREAM OR GEL FOR PROLONGING THE EFFECT OF PERFUME-FRAGRANCE ON A PERSON

This is a continuation of co-pending application Ser. No. 758,882, filed on July 25, 1985.

BACKGROUND OF THE INVENTION

The present invention is directed to a cream or gel for application on the skin of a person before the application thereto of perfume, cologne, toilet water, and the like, in order to prolong the lasting power of the fragrance contained in the perfume.

Compounds are known that are used to make fragrances in perfumes and colognes last longer. These compounds are called fixatives, and are provided in the perfume or cologne itself for application to the skin together. Examples of such prior art products are disclosed in U.S. Pat. Nos. 3,939,099 and 4,264,478. The fixatives in each of these patents attempt to prolong the period during which the perfume or cologne exudes its fragrance on the person as, by example, encapsulating or forming a film. However, these prior art products are limited in scope and use, and are expensive to make since the essential ingredients for providing fixation are expensive. Further, as in the case of U.S. Pat. No. 3,939,316, a water-alcohol solvent is necessary.

SUMMARY OF THE INVENTION

It is the primary objective of the present invention to provide an odorless, unscented cream or gel that can be applied on the skin of a person before the application of a perfume or cologne, in order to enhance and prolong the fragrance emanating from the applied perfume or cologne.

It is another objective of the present invention to provide a gel or cream that is easily absorbed into the skin, yet will provide volatility-reduction to the perfume or cologne applied thereupon.

It is yet another objective of the present invention to provide a cream or gel that also acts as an emollient, and soothes the skin while at the same time prolongs the fragrance-emanation of the perfume.

It is still another objective of the present invention to provide a method of using the cream or gel to prolong the fragrance-emanation of the applied perfume.

It is another objective of the present invention to provide a method of masking the novel gel or cream of the invention.

Toward these and other ends, the cream or gel of the present invention consists of squalane, which is a colorless, odorless, tasteless, transparent, stable, inert homogeneous liquid oil, in the range of between 5-15%, by weight. Other ingredients include an emulsifying agent in the amount of between 10-20%, an emollient in the amount of between 5-20%, water in the amount between 50% and 75%, and preservative in the amount of between 0.2% and 2%. Water in the amount of between 50% and 65% is also included.

The compound is made by first mixing together the water preservative, and heating them to approximately 75° C. The other ingredients are mixed separately but simultaneously at 75° C. Thereafter, the second mix is slowly added to the first mix, with rapid agitation for about 5 minutes. The entire mixture is then allowed to cool to approximately 40° C., at which point color may be added. After allowing it to cool to 35° C., the product is ready for packaging.

The novel method of using the present invention is to first apply a thin coating thereon on the skin of the person where the perfume or cologne is to be applied, such that the skin absorbs part of the composition. Thereafter, the perfume, or cologne, is applied thereupon, thus rendering an application of perfume or cologne that is longer-lasting than if the compound of the present invention were not used first.

DETAILED DESCRIPTION OF THE INVENTION

The cream or gel of the present invention is used before the application of perfume, cologne, or the like on the skin of a person, so that the perfume itself is applied over the cream, to thus prolong the fragrance-emanating time period of the applied perfume. The cream or gel is a compound having as one of its basic ingredients a very-long chain, saturated hydrocarbon in the lipid family. In the preferred embodiment, squalane is used, which is a hydrocarbon of next-to-the-longest chain in the lipid family.

Squalane is also known as spinacane, dodecahydrosqualene, perhydrosqualene, and 2,6,10,15,19,23Hexamethyltetracosane. It is tasteless, odorless, colorless, transparent, and stable, inert homogeneous liquid oil that is non-toxic, non-irritating, hypoallergenic, non-sensitizing, and non-oxidizing. It is a normal constituent of the human sebum, and is the next-to-the longest chain of saturated hydrocarbon lipids. In the preferred formula of the present invention, squalane is provided in the range of between approximately 5% to 10%, by weight, of finished product.

Instead of using squalane, squalene may be used, which is the longest chain of hydrocarbon lipids. In combination with the hydrocarbon lipid, there is also included water solvent, preservative, emollient, and emulsifying agent. In a preferred formula of the present invention, the following ingredients, by percentage weight, have been found to be most effective in prolonging the fragrance-emitting power of a perfume or cologne on the person, with the period of time during which such fragrance-transmittance occurs being substantially increased by the order of 50% for some perfumes and colognes.

EXAMPLE I

| INGREDIENT | PERCENTAGE WEIGHT |
| --- | --- |
| Water | 69% |
| "Germaben II" | 1% |
| Squalane | 5% |
| Emulsifying Wax | 11% |
| Glycerin | 5% |
| "Arlacel 165" | 6% |
| Isopropyl Myristate | 3% |

"Germaben II" is a perservative made by Sutton Laboratories, Inc. and includes three separate preservatives: methylparaben, propylparaben, and germall 115. Any two of these separate preservatives may be used alone in the present invention, as well as other suitable and equivalent preservatives. The emulsifying wax provides a thick consistency to the final product, so that it reduces the volatility of the applied perfume applied thereon in combination with the squalane. The "Arlacel 165" is another emulsifier, containing glycerol stearate and PEG-100 Stearate. Equivalent and suitable other lighter emulsifying agents may be used instead. The isopropyl myristate and glycerin are emollients or humectants, with the isopropyl myristate being a light emollient, and the glycerin being a heavy emollient. Instead of the use of isopropyl myristate, mineral oil may used.

In another formula of the present invention, where a red dye is used, the following shows the proportion of ingredients.

EXAMPLE II

| INGREDIENT | PERCENTAGE WEIGHT |
|---|---|
| Water | 66% |
| "Germaben II" | 1% |
| Squalane | 10% |
| Emulsifying Wax | 10% |
| Glycerin | 5% |
| "Arlacel 165" | 5% |
| Isopropyl Myristate | 3% |
| D & C Red Dye #19 | qs. |

In Example III, the squalane has been replaced by squalene, with the following percentages of ingredients:

EXAMPLE III

| INGREDIENT | PERCENTAGE WEIGHT |
|---|---|
| Water | 66% |
| "Germaben II" | 1% |
| Squalane | 10% |
| Emulsifying Wax | 10% |
| Glycerin | 5% |
| "Arlacel 165" | 5% |
| Isopropyl Myristate | 3% |
| D & C Red Dye #19 | qs. |

To make each of the above formulae, the water and preservative are mixed together and heated to approximately 75° C. Simultaneously therewith, the other ingredients are mixed and heated at the same temperature. After thorough mixing, the second mix is added slowly to the first water-and-preservative mix with rapid agitation for about five minutes. Thereafter, the entire mixture is allowed to cool under moderate agitation, whereupon at 40° C. color may be added thereto. At 35° C., the compound is ready for packaging.

When using any of the formulae of the present invention, a layer thereof is first rubbed onto a portion of the skin of the person until at least some of the cream or gel is absorbed into the skin, whereupon the perfume or cologne is applied thereon. The perfume or cologne is not applied directly onto the skin when using the product of the present invention. The product of the present invention and its method of use are ideal for use also in what is termed "layering". Layering is the process by which a woman enhances the fragrance-producing power of her perfume by first bathing in bath water containing therein bath oils or powders having the same general fragrance as the perfume she is later to apply on her skin. By successive treatments of aromatizing her skin, the final application of the perfume is enchanced thereby. Since the product of the present invention is odorless and unscented, the use thereof does not interfere with the technique of layering, as would other creams and gels. Further, the product of the present invention is made such that any fragrance applied thereon is not only prolonged in its exudation, but is also enhanced such that its clarity and intensity is increased, for reasons not totally understood.

While specific formulae have been described, it is to be understood that numerous modifications may be made therein without departing from the scope, spirit and intent of the invention. For example, roll-ons or liquid sprays may readily be adopted from the above-formulae.

What is claimed:

1. A gel or cream compound for application onto the skin of a person for serving as a base layer for the application thereupon of a perfume, cologne, or the like, comprising the following ingredients by percentage weight:
   water in the range of between approximately 50% and approximately 75%;
   emulsifying wax in the range of between 10% to 12%;
   a light emulsifying agent in the range of between approximately 3% and approximately 6%;
   emollient in the range of between approximately 5% and approximately 15%;
   squalane in the range of between approximately 4% and approximately 11%; and
   a preservative.

2. The gel or cream according to claim 1, wherein said preservative is in the range of between 0.2% and 2%.

* * * * *